United States Patent [19]
Gondo

[11] Patent Number: 5,431,169
[45] Date of Patent: Jul. 11, 1995

[54] ULTRASONIC DIAGNOSING APPARATUS

[75] Inventor: Masahiko Gondo, Tokyo, Japan

[73] Assignee: Olympus Optical Co., Ltd., Tokyo, Japan

[21] Appl. No.: 99,359

[22] Filed: Jul. 30, 1993

[30] Foreign Application Priority Data

Aug. 3, 1992 [JP] Japan ................................. 4-206630
Aug. 5, 1992 [JP] Japan ................................. 4-209038

[51] Int. Cl.⁶ .............................................. A61B 8/00
[52] U.S. Cl. .............................................. 128/661.09
[58] Field of Search ................ 128/660.07, 660.10, 128/661.01, 661.08, 661.09, 661.10

[56] References Cited

U.S. PATENT DOCUMENTS

| | | | |
|---|---|---|---|
| 4,961,427 | 10/1990 | Namekawa . | |
| 5,103,827 | 4/1992 | Smith | 128/661.08 |
| 5,170,792 | 12/1992 | Sturgill et al. | 128/661.09 |
| 5,186,177 | 2/1993 | O'Donnell et al. | 128/661.01 |
| 5,188,113 | 2/1993 | Sato et al. | 128/661.09 |
| 5,211,169 | 5/1993 | Freeland | 128/661.10 |
| 5,269,308 | 12/1993 | Hagiwara et al. | 128/661.09 |

FOREIGN PATENT DOCUMENTS

0346890A1 12/1989 European Pat. Off. .
0430093A3 6/1991 European Pat. Off. .
0535962A1 4/1993 European Pat. Off. .

*Primary Examiner*—George Manuel
*Attorney, Agent, or Firm*—Stevens, Davis, Miller & Mosher

[57] ABSTRACT

The ultrasonic diagnosing apparatus including an ultrasonic probe, an ultrasonic wave transmitting and receiving unit for transmitting ultrasonic pulses toward a living body and receiving ultrasonic waves reflected by the living body to produce an echo signal, and a signal processing circuit for processing the echo signal such that a Doppler frequency representing a relative movement between the ultrasonic probe and living tissues is detected and a velocity of a blood stream which is free from the influence of the relative movement is detected on the basis of the Doppler frequency due to the relative movement between the ultrasonic probe and the living tissues. In a power spectrum distribution, the Doppler frequency can be detected as a peak frequency at which the magnitude of the power spectrum becomes maximum. In one embodiment of the ultrasonic diagnosing apparatus, the frequency axis of the power distribution is shifted such that the Doppler frequency becomes zero, and finally a Doppler frequency due to the blood stream is detected from a power spectrum component outside a cut-off frequency range. In a second embodiment, a first Doppler frequency due to the blood stream is detected from a signal component which is obtained by MTI filters and auto-correlation circuits, a second Doppler frequency due to the relative movement between the ultrasonic probe and the living tissues is detected from a signal component which is obtained by the auto-correlation circuits, and then a velocity of the blood stream is detected from a difference between the first and second Doppler frequencies.

25 Claims, 14 Drawing Sheets

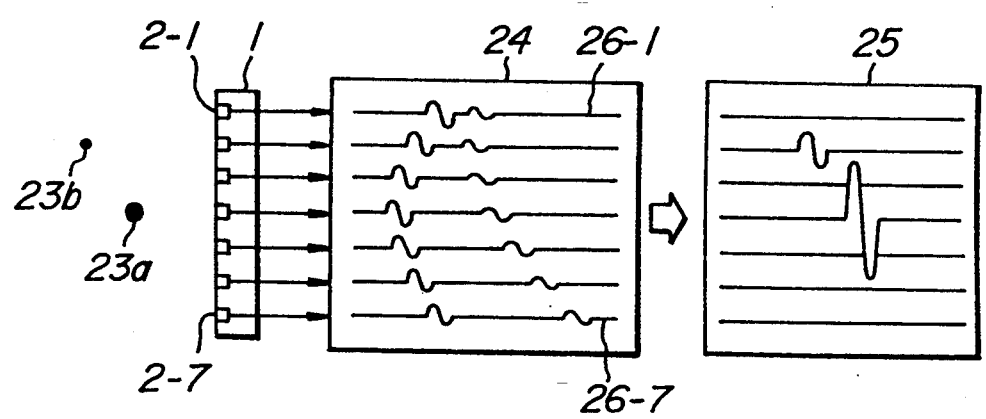
FIG_2

FIG_3A
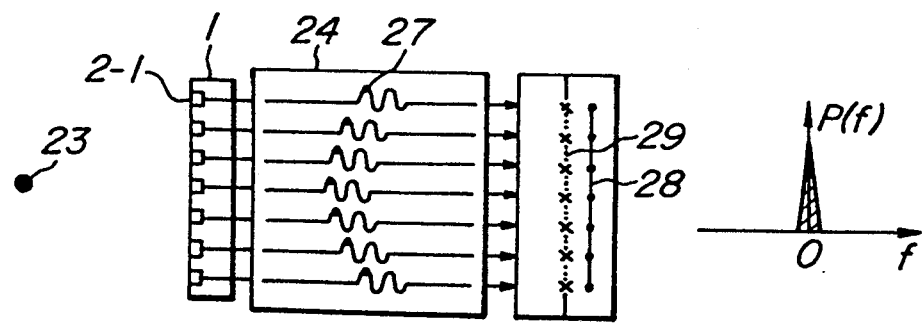
FIG_3B
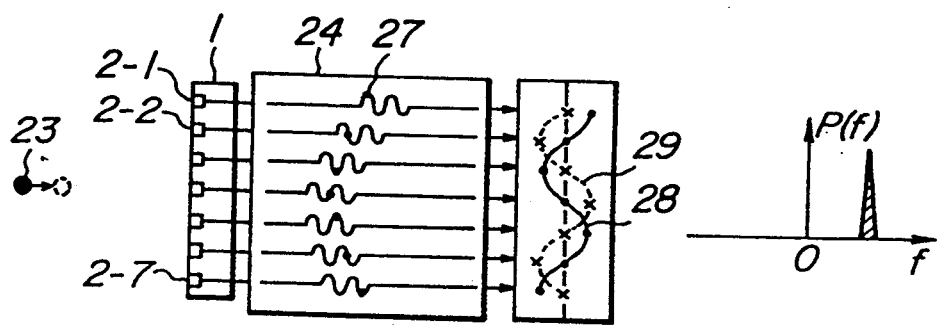
FIG_3C
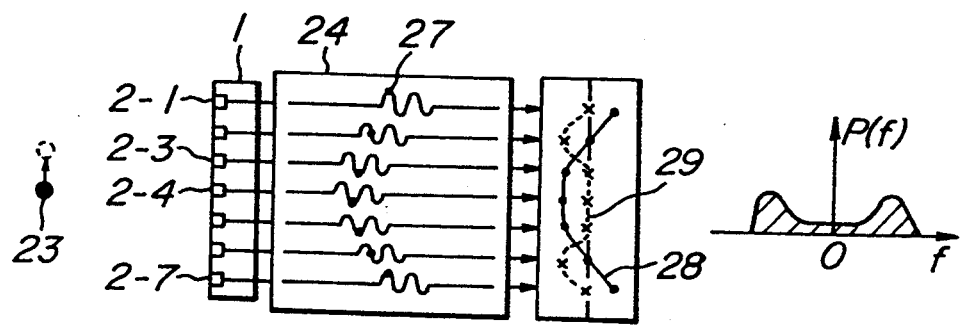

FIG_4
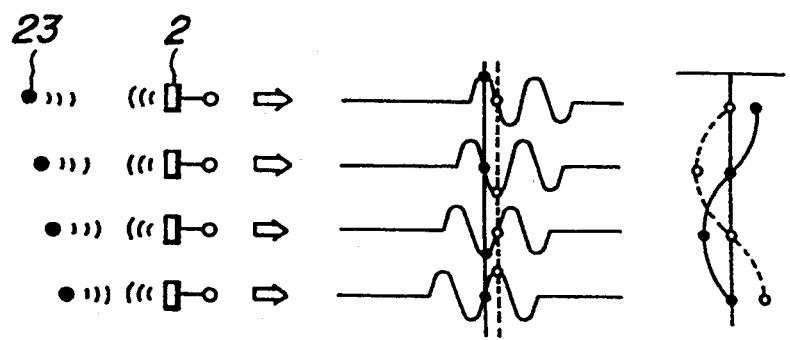

FIG._5A
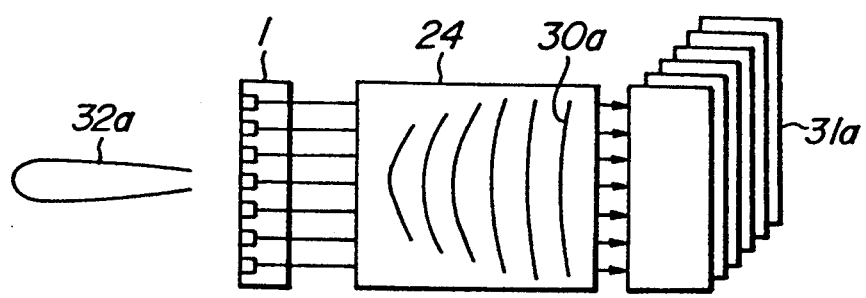
FIG._5B
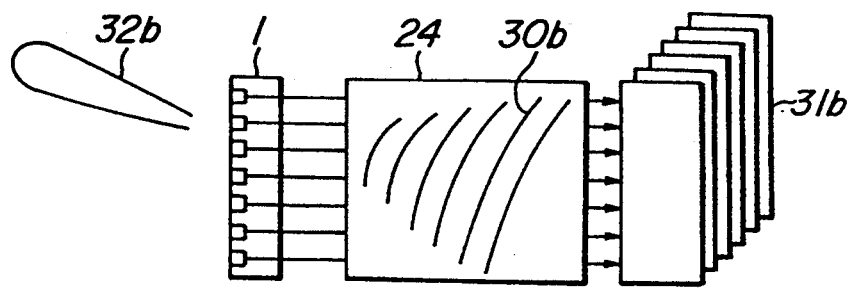
FIG._5C
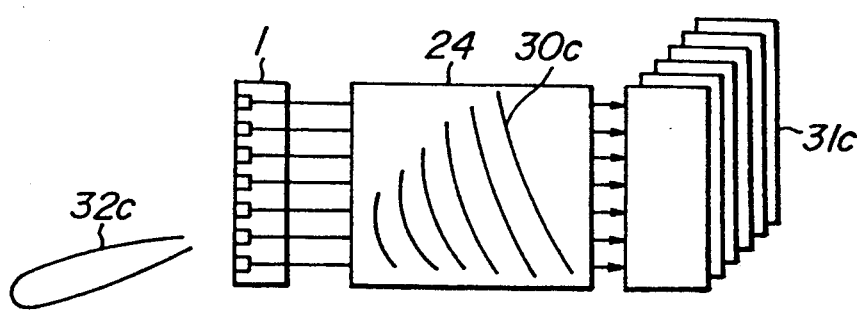

FIG_6A
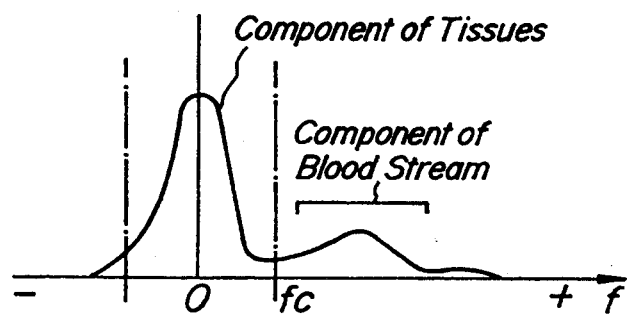
FIG_6B
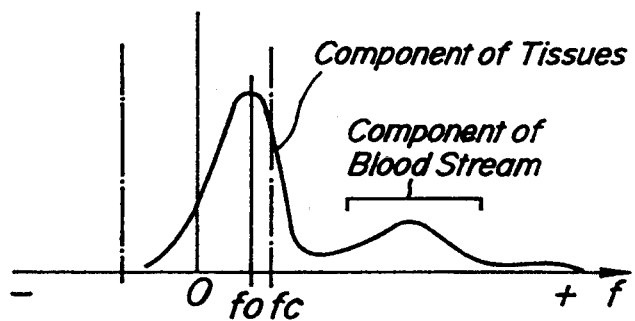
FIG_6C
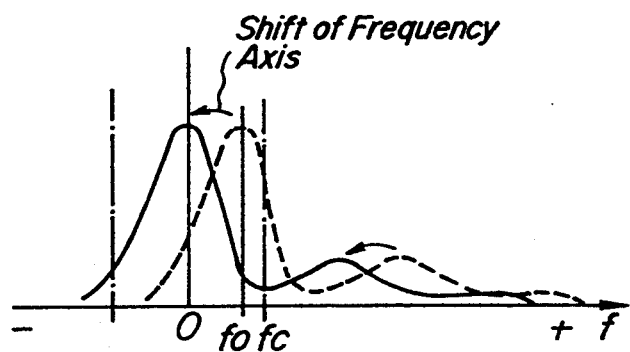

FIG_7
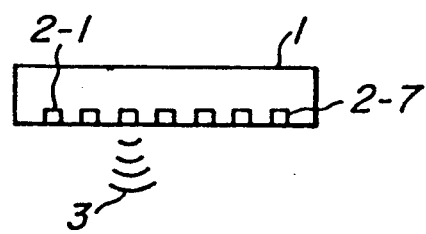
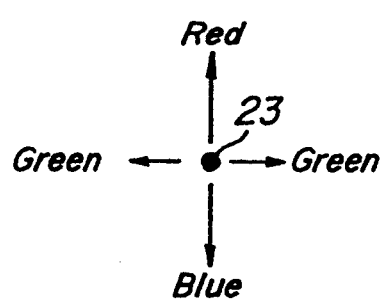
FIG_8
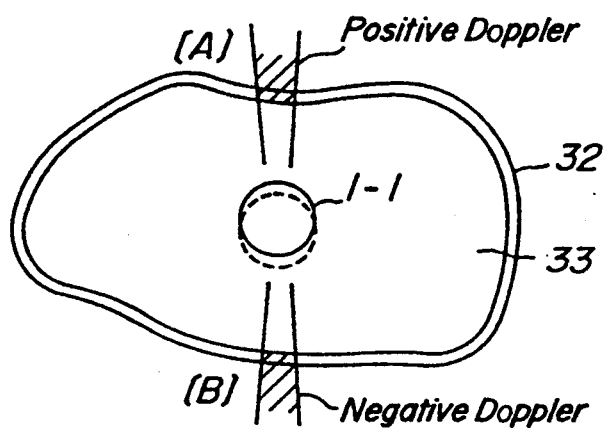

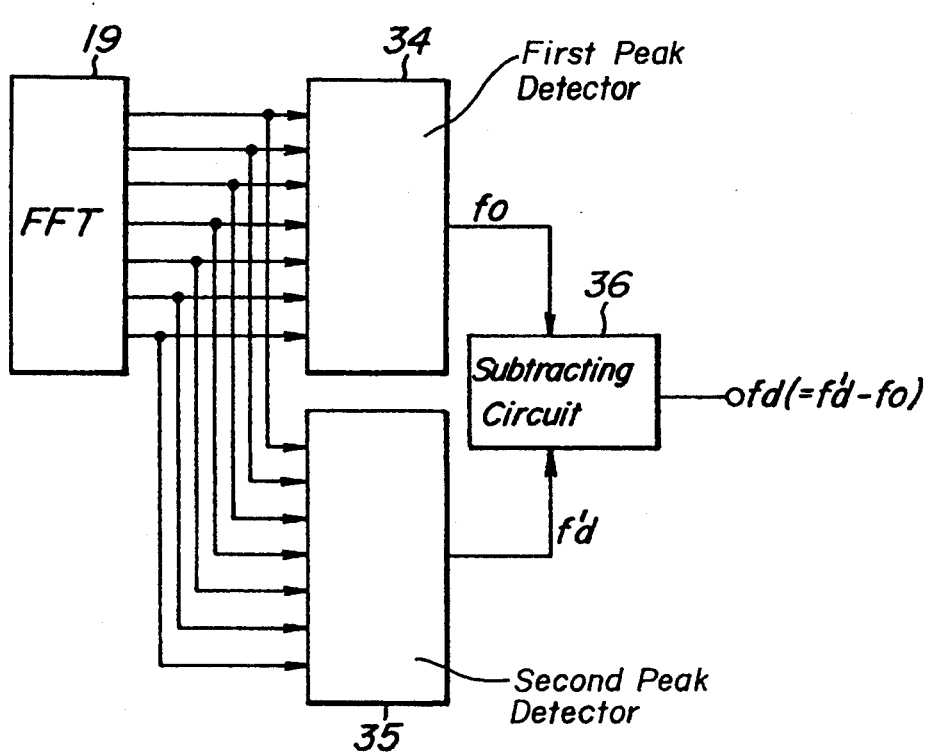
FIG_10

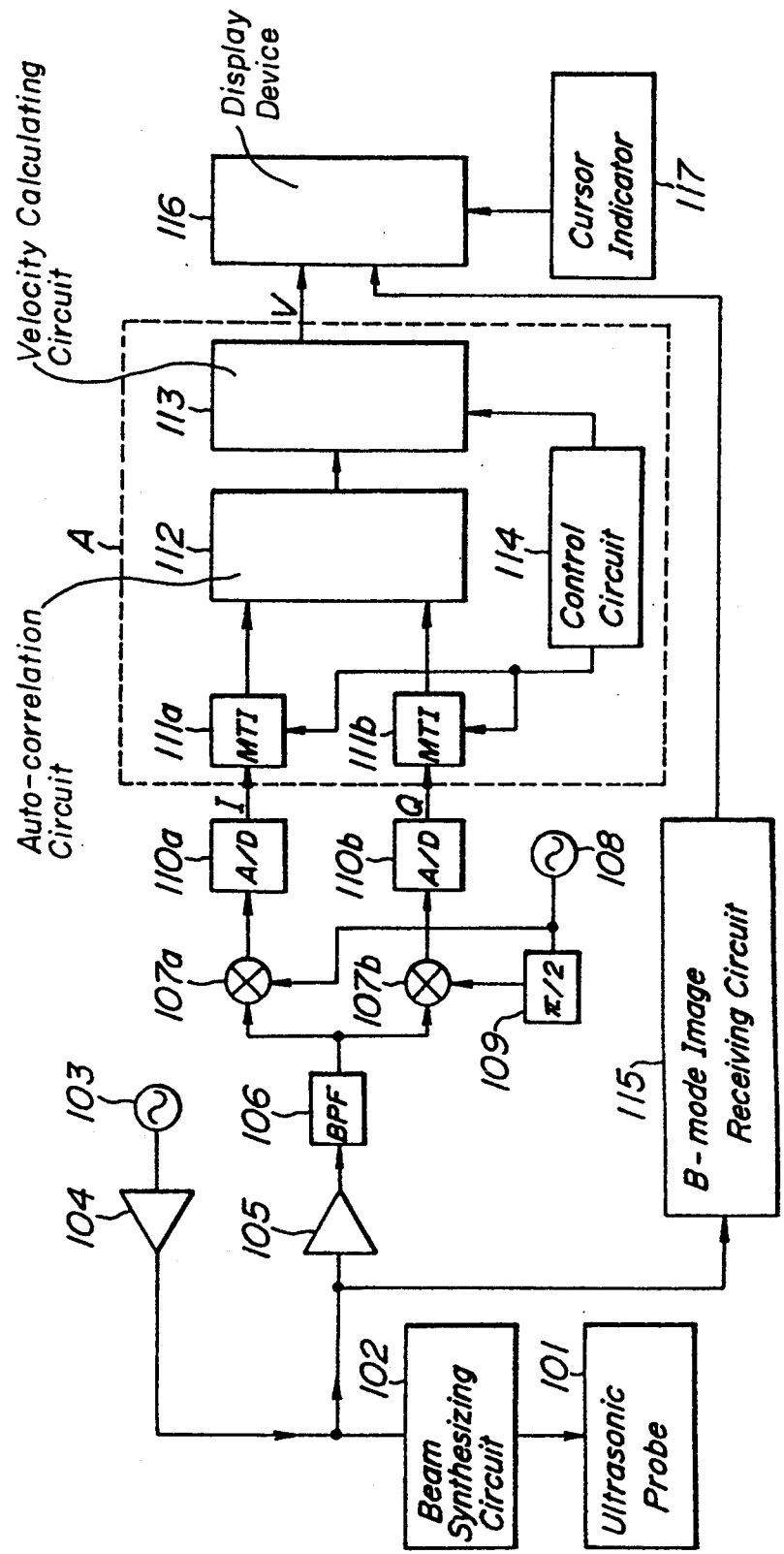

FIG_12
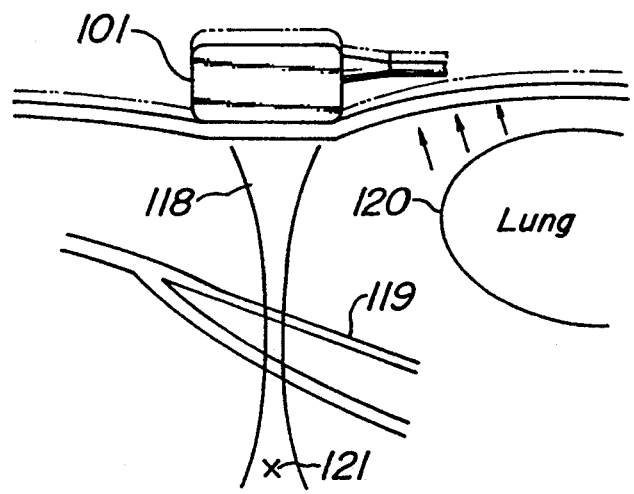
FIG_13A
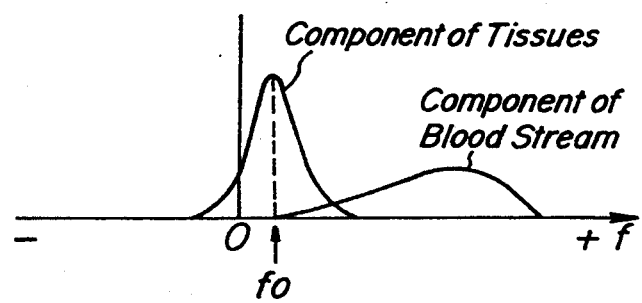
FIG_13B
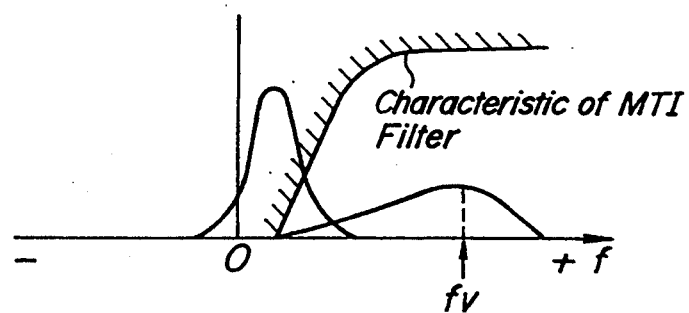

FIG_15

ULTRASONIC DIAGNOSING APPARATUS

BACKGROUND OF THE INVENTION

1. Field of the Invention

The present invention relates to an ultrasonic diagnosing apparatus for measuring a velocity of a blood stream within a living body by emitting ultrasonic pulses having a given repetition frequency toward the living body, receiving ultrasonic waves reflected by the living body to derive an echo signal and detecting a Doppler shift contained in the echo signal.

2. Description of the Related Arts

There has been known an ultrasonic diagnosing apparatus for measuring a velocity of a blood stream by utilizing the Doppler effect upon the ultrasonic wave and displaying the blood stream on a color monitor in superimposition upon an ultrasonic image. That is to say, when the ultrasonic wave is transmitted toward the blood stream and the ultrasonic wave is reflected by blood cells flowing within a blood vessel, the ultrasonic wave is subjected to the Doppler shift. Such an apparatus is called a color Doppler apparatus and has been widely used. The color Doppler apparatus is described in, for instance, Japanese Patent Application Laid-open Publication Kokai Sho 58-188433 and U.S. Pat. No. 4,799,490. In principle, in such a color Doppler apparatus, a burst-pulsatory ultrasonic beam is emitted from an ultrasonic vibrating element array with a constant time interval and a time period from an instant at which the ultrasonic beam is emitted toward an object to a timing at which an ultrasonic wave reflected by the object is received by the ultrasonic vibrating element array is detected to measure a position of the object within the space and at the same time a frequency shift of the transmitting burst pulse signal is detected to measure a movement of the object within the space. Initially the color Doppler apparatus was used to diagnose the circulation system of the human being such as a heart, but recently it has been utilized to diagnose other organs such as stomach due to the fact that the color Doppler apparatus can provide a large amount of useful information.

In the known color Doppler apparatus, a velocity of the blood stream is detected by utilizing the Doppler effect, so that it is impossible to detect a velocity component of the blood stream in a direction perpendicular to the ultrasonic beam. Moreover, in order to measure a blood stream having a low velocity, it is necessary to set a special Doppler sequence for emitting an ultrasonic wave pulse having a longer time duration than that of an ultrasonic wave pulse for obtaining a usual B-mode ultrasonic image, and further in order to obtain a Doppler signal having a high quality, it is necessary to repeat the Doppler sequence about ten times and to perform an averaging process. This results in a great decrease in a frame rate as compared with the B-mode ultrasonic image and the spatial resolution is also reduced.

In copending U.S. Patent application Ser. No. 07/953,811, there is proposed a novel ultrasonic diagnosing apparatus which can measure a low velocity of a blood stream flowing in a direction parallel with a plane of an ultrasonic probe at a very high spatial resolution without reducing the frame rate by utilizing the improved synthetic aperture method.

The inventor of the instant application has conducted various experiments for the above mentioned ultrasonic diagnosing apparatus utilizing the improved synthetic aperture method and has found the following problems. Particularly, when a blood stream having a very low velocity is measured, relative movement between an ultrasonic probe and an object under observation due to movement of a patient body, breathing and movement of the ultrasonic probe can not be ignored, and Doppler shifts are produced not only by the movement of blood cells within a blood vessel, but also by ordinary or stationary living tissues surrounding the blood vessel. Therefore, a displayed image is wholly colored in blue or red and it is difficult to detect the blood stream easily and accurately. In order to avoid such a drawback, the patient is required to stop breathing during the Doppler sequence, but it is apparent that such a solution is a substantial burden to the patient.

Moreover, also in the usual ultrasonic diagnosing apparatus in which the synthetic aperture method is not utilized, the above mentioned problem of the relative movement between the ultrasonic probe and the living tissues equally occurs, so that it is difficult to measure the blood stream having a low velocity in an easy and reliable manner. Particularly, in an ultrasonic endoscope in which the ultrasonic probe is arranged within a distal end of an insertion section of the endoscope, it is quite difficult to fix the distal end of the insertion section within the patient, and thus the ultrasonic probe is liable to move, so that a velocity of the blood stream can not be measured reliably.

SUMMARY OF THE INVENTION

The present invention has for its object to provide a novel and useful ultrasonic diagnosing apparatus, in which a velocity of a blood stream can be reliably measured without being affected by the relative movement between the ultrasonic probe and the living tissues.

An ultrasonic diagnosing apparatus according to the invention comprises:

ultrasonic wave transmitting and receiving means including an ultrasonic probe for emitting ultrasonic waves toward a living body and receiving ultrasonic waves reflected by the living body to produce an echo signal; and a signal processing circuit for processing the echo signal generated from the ultrasonic wave transmitting and receiving means such that a Doppler frequency contained in the echo signal due to a relative movement between the ultrasonic probe and living tissues of the living body is detected and a velocity of a blood stream is detected in accordance with the Doppler frequency without being influenced by the relative movement between the ultrasonic probe and the living tissues.

In the ultrasonic diagnosing apparatus according to the invention, a Doppler frequency due to the blood stream can be detected by removing the influence of the Doppler frequency due to the relative movement between the ultrasonic probe and the living tissues, and thus the velocity of the blood stream can be measured efficiently and accurately.

In a preferable embodiment of the ultrasonic diagnosing apparatus according to the invention, the ultrasonic probe is formed by a plurality of ultrasonic vibrating elements arranged in an array and groups of ultrasonic pluses having a given repetition frequency are successively emitted from these ultrasonic vibrating elements and ultrasonic waves reflected by the living body are received by these elements to produce echo signals. The signal processing circuit is constructed to process these echo signals to derive a power spectrum distribution of the spatial frequency in accordance with the synthetic aperture method, and then the Doppler frequency due the relative movement between the ultrasonic probe and the living tissues is detected. Finally, the velocity of the blood stream is detected in accordance with the Doppler frequency without being affected by the relative movement.

In another preferable embodiment of the ultrasonic diagnosing apparatus according to the invention, the ultrasonic probe is formed by a plurality of ultrasonic vibrating elements arranged in an array and groups of ultrasonic wave pulses having a given repetition frequency and being delayed by predetermined delay times are emitted from the ultrasonic vibrating elements. Ultrasonic waves reflected by the living body are received by the ultrasonic vibrating elements and output signals from these elements are delayed by predetermined delay times to produce the echo signal. Then, the echo signal is converted into a complex signal by means of an orthogonal detection circuit, and an auto-correlation of the complex signal is derived by the auto-correlation circuit. Next, the Doppler frequency due to the relative movement between the ultrasonic probe and the living tissues is detected from outputs of the auto-correlation circuit, and a velocity of the blood stream which is free from the influence of the relative movement is detected in accordance with the Doppler frequency. To this end, the signal processing circuit comprises means for detecting a first Doppler frequency as an average frequency of the power spectrum of the echo signal and a second Doppler frequency due to the blood steam by removing a power spectrum component corresponding to a reflection from the stationary living tissues, and means for measuring a velocity of the blood stream as a difference between the first and second Doppler frequencies.

In another preferable embodiment of the ultrasonic diagnosing apparatus according to the invention, a distribution of the detected velocity of the blood stream is displayed by three primary colors such that a velocity component of the blood stream which flows toward the ultrasonic probe is displayed in a first primary color such as red, a velocity component of the blood steam which flows away from the ultrasonic probe is displayed in a second primary color such as blue, and a velocity component of the blood steam which flows in parallel with the ultrasonic probe is displayed in a third primary color such as green. In this manner, a two dimensional movement of the blood stream can be displayed by the three primary colors, and the user can recognize the distribution of the velocity of the blood stream easily.

BRIEF DESCRIPTION OF THE DRAWINGS

FIG. 2 is a schematic view for explaining the conception of the synthetic aperture method;

FIGS. 3A, 3B and 3C are schematic views representing the principle of detecting the movement of an object by utilizing the Doppler effect;

FIG. 4 is a schematic view for explaining the conception of the deviation in phase wave front due to the movement of the object;

FIGS. 5A, 5B and 5C are schematic views for explaining the conception for changing the directivity of the ultrasonic wave;

FIGS. 6A, 6B and 6C are schematic views for explaining the manner of compensating the movement of the ultrasonic probe;

FIG. 7 is a schematic view illustrating the manner of displaying the movement of the blood stream in various colors;

FIG. 8 is a schematic view for explaining the manner of compensating the movement of the ultrasonic probe having circularly arranged ultrasonic vibrating elements;

FIG. 10 is a block diagram showing a portion of a modification of the embodiment shown in FIG. 1;

FIG. 11 is a block diagram representing the whole construction of another embodiment of the ultrasonic diagnosing apparatus according to the invention;

FIG. 12 is a schematic view showing the manner of measuring the blood stream by the apparatus according to the invention;

FIGS. 13A and 13B are schematic views illustrating the principle of measuring the blood stream according to the invention;

DESCRIPTION OF THE PREFERRED EMBODIMENTS

Figure 1:
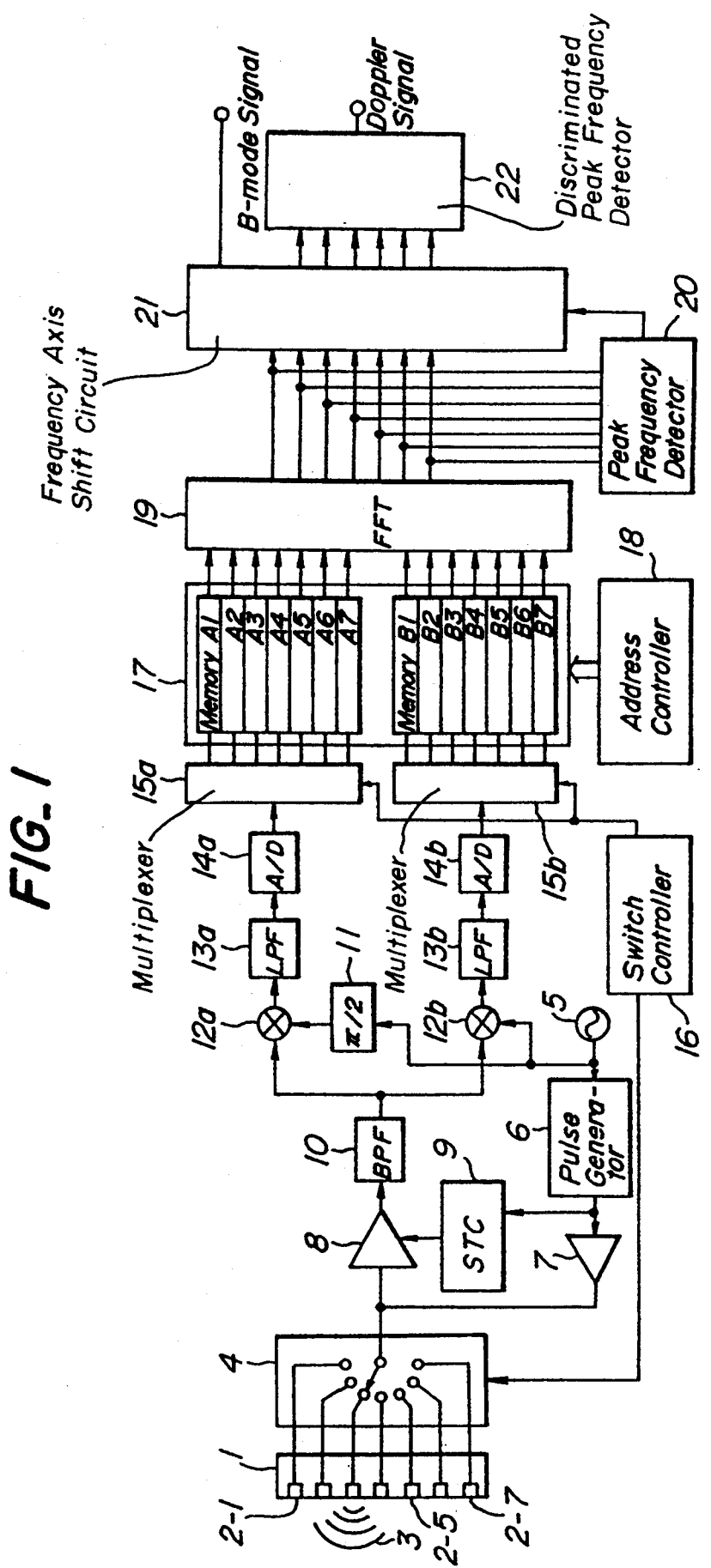
FIG. 1 is a block diagram showing the whole construction of an embodiment of the ultrasonic diagnosing apparatus according to the invention.

FIG. 1 is a block diagram showing the construction of the ultrasonic diagnosing apparatus according to the invention. The ultrasonic diagnosing apparatus comprises an ultrasonic probe 1 having a plurality of ultrasonic vibrating elements 2-1 to 2-7 for emitting ultrasonic waves 3, a distal end multiplexer 4 for selectively switching the ultrasonic vibrating elements 2-1 to 2-7, a signal generator 5, a pulse generator 6, a transmitting amplifier 7, a receiving amplifier 8, STC (sensitivity time control) circuit 9 for controlling an amplification level of the receiving amplifier 8, a band pass filter (BPF) 10, a 90-degree ($\pi/2$) phase shifter 11, low pass filters (LPF) 12$a$, 12$b$, multipliers 13$a$, 13$b$, A/D converters 14A, 14B, multiplexers for memory 15$a$, 15$b$, a switching control circuit 16 for controlling the distal end multiplexer 4 and memory multiplexers 15$a$, 15$b$, a wave surface memory unit 17, an address control circuit 18, a fast Fourier transformer (FFT) 19, a peak frequency detection circuit 20, a frequency axis shift circuit 21, and a discriminated peak frequency detection circuit 22. The wave surface memory unit 17 comprises real part wave surface memories A1 to A7 and imaginary part wave surface memories B1 to B7, each pairs of the memories A1, B1; A2, B2;---A7, B7 corresponding to respective ultrasonic vibrating elements 2-1 to 2-7.

In the present embodiment, at first, the distal end multiplexer 4 and memory multiplexers 15$a$, 15$b$ are set to connect a first ultrasonic vibrating element 2-1 and a first pair of wave surface memories A1, B1 into a circuit under the control of the switching control circuit 16. Then, the pulse generator 6 is triggered to produce a series of transmission pulses in synchronism with an output signal of the signal generator 5 for a given time period. These transmission pulses are supplied via the transmitting amplifier 7 and distal end multiplexer 4 to the ultrasonic vibrating element 2-1, so that this element emits a series of ultrasonic pulses 3 toward the living body. In the present embodiment, the ultrasonic probe 1 is arranged within a distal end of an insertion section of an endoscope, and thus the ultrasonic probe is inserted into a cavity of a patient. The ultrasonic pulses 3 are reflected by living tissues and blood cells within blood vessels and reflected ultrasonic waves are received by the ultrasonic vibrating element 2-1. Then, the ultrasonic waves are converted by the element 2-1 into electric signals. The thus generated electric signals are supplied via the distal end multiplexer 4 to the receiving amplifier 8 and are amplified thereby to a suitable signal level. In this case, the amplitude of the electric signal generated by the ultrasonic vibrating element becomes smaller when an object which reflects the ultrasonic wave is far from the ultrasonic probe 1, so that the amplification of the receiving amplifier 8 is increased in accordance with time by the STC circuit 9 in a usual manner.

Undesired noise contained in an output signal of the receiving amplifier 8 is removed by the BPF 10 and then an output signal of the BPF is supplied to an orthogonal detection circuit comprising the multipliers 12a, 12b, LPFs 13a, 13b and $\pi/2$ phase shifter 11. Then, the electric signal is converted into a complex signal g(t, x) in a base band region and represented by the following equation (1):

$$g(t, x) = a(t, x) + jb(t, x) \quad (1)$$

In this equation, a(t, x) represents a real part, b(t, x) denotes an imaginary part, and x represents a position of an ultrasonic vibrating element.

The real and imaginary parts of the complex signal are then supplied to the A/D converters 14a and 14b, respectively and are converted thereby into digital signals. The thus converted digital signals are supplied via the multiplexers 15a and 15b to the real part wave surface memory A1 and imaginary part wave surface memory B1, respectively and are stored therein as time sequential data.

The above mentioned operation is repeated until a set of the wave surface data obtained by using the ultrasonic vibrating elements 2-1 to 2-7 has been stored in the memories A1 to A7 and B1 to B7 of the memory unit 17. Next, the thus stored wave surface data is processed by the synthetic aperture method to synthesize or compose ultrasonic images in respective spaces.

FIG. 2 is a schematic view showing the synthetic aperture method. Reference numerals 23a, 23b denote objects or substances which reflect the ultrasonic wave, 24 a wave surface memory, and 25 represents a synthesized wave surface. When the ultrasonic pulses are emitted by the ultrasonic vibrating element 2-1 in the ultrasonic probe 1, a wave surface signal 26-1 is stored in a wave surface memory 24. Similarly, in the wave surface memory 24, there are successively stored wave surface signals 26-2 to 26-7 by using the ultrasonic vibrating elements 2—2 to 2-7. It should be noted that positional relations in the space between respective ultrasonic vibrating elements 2-1 to 2-7 and the objects 23a and 23b are different from one another, so that the wave surface signals 26-1 to 26-7 have different shapes from one another. Therefore, by combining these wave surface signals 26-1 to 26-7 with each other after suitably delaying or advancing the signals such that the ultrasonic pulses generated by the ultrasonic vibrating elements 2-1 to 2-7 are focused at any desired point in the space, it is possible to provide the directivity for the ultrasonic pulse like as the known beam composing method using delay circuits. This method is called the Delay and Sum method. Therefore, by processing the wave surface signals for all points in the space, it is possible to detect the distribution of the substances in the space.

It should be noted that each of the ultrasonic vibrating elements 2-1 to 2-7 has a broad directivity and a low directivity resolution, but by utilizing the wave surface synthesizing method, the effective directivity of the vibrating element can be sharpened and the directivity resolution can be improved to a large extent. In other words, a very sharp directivity obtained by using a vibrating element having a large aperture can be obtained by moving a vibrating element having a small aperture in the space to detect the wave surface signals and by synthesizing these wave surface signals. Therefore, this method is called the synthetic aperture method.

Next a principle for detecting a moving object will be explained with reference to FIGS. 3A, 3B and 3C. FIG. 3A shows a situation in which a stationary object 23 is existent in the space, and a set of time sequential data is stored in the wave surface memory 24 by repeating the above mentioned transmitting and receiving operations. The thus stored time sequential data is sampled at sampling points indicated by dots 27 in accordance with the position of the object 23 within the space, there is obtained a set of spatial data at a certain time instance as indicated by solid line 28. Next the time sequential data is sampled at sampling points whose phase at the center frequency is delayed by 90 degrees with respect to the first sampling points 27 to derive a set of spatial data denoted by a dotted line 29. These sets of spatial data denoted by the solid and dotted lines 28 and 29 may be expressed by a complex signal. A periodic variation in the frequency of the spatial data is called a spatial frequency. In the condition illustrated in FIG. 3A, the spatial frequency mainly consists of a DC component, because the object 23 is stationary. When the spatial data is processed by the FFT 19, there is obtained a spatial frequency spectrum or power spectrum P(f) is obtained, or shown in FIG. 3A. This spatial spectrum indicates data at one point within the space.

FIG. 3B represents a case in which an object 23 is moving toward the ultrasonic probe 1. While the ultrasonic vibrating elements 2-1 to 2-7 are scanned successively, a distance between the object 23 and the ultrasonic probe 1 becomes shorter and thus the wave surface data stored in the wave surface memory 24 is deviated from that shown in FIG. 3A. When the wave surface data is sampled at the same sampling timings 27, a signal component having a periodic component is detected. When this periodic signal component is Fourier-transformed by the FFT 21, a spatial spectrum having a peak in a positive frequency range is derived.

FIG. 4 is a schematic view explaining the phenomenon in which the wave surface data is deviated in accordance with the movement of the object 23. When the object 23 moves toward an ultrasonic vibrating element 2 in the ultrasonic probe 1, a distance between the object and the vibrating element becomes shorter and shorter, so that a time instance at which the ultrasonic wave reflected by the object 23 arrives at the vibrating element 2 becomes gradually earlier. Therefore, when the signal is sampled at the same timing, the movement of the object results in the change in a phase of the sampled signal. According to the present embodiment, the signal is sampled at two sampling points which are separated from each other by 90 degrees and a complex signal is derived. A phase of this complex signal is changed in accordance with the movement of the object 23.

FIG. 3C is a schematic view depicting a case in which the object 23 moves in a direction parallel with the ultrasonic probe 1, i.e. in a direction perpendicular to the propagating direction of the ultrasonic pulse. In such a case, for the ultrasonic vibrating elements 2-1 to 2-3, a spatial distance is gradually decreased, while for the ultrasonic vibrating elements 2-4 to 2-7, a spatial distance is gradually increased. Therefore, a signal having positive and negative frequency components is obtained when the signal is sampled at the same timings as in the cases shown in FIGS. 3A and 3B. These positive and negative frequency components can be distinguished from each other in the complex signal. Therefore, when the signal is processed by the FFT 19, a spectrum distribution having the positive and negative components is detected.

When the object 23 moves away from the ultrasonic probe 1, the situation is reversed to the case shown in FIG. 3B and the negative frequency component may be obtained as the result of the Fourier transform. Furthermore, when the object moves parallel with the ultrasonic probe in a direction opposite to that illustrated in FIG. 3C, a phase spectrum reverse to that shown in FIG. 3C is obtained, so that the direction of the movement of the object can be detected.

In the above explanation, for the sake of simplicity, in order to detect the complex signal constituting the reflection signal at a certain focal point, the wave surface signal is sampled at two sampling points which are separated from each other by 90 degrees. However, in order to derive the complex signal, it is common to use an orthogonal detector comprising the multipliers 12a, 12b, LPFs 13a, 13b and 90-degree phase shifter 11 as illustrated in FIG. 1.

FIGS. 5A, 5B and 5C are schematic views showing the principle of changing the directivity of the ultrasonic beam. In FIG. 5A, an ultrasonic beam 32a is projected in a direction perpendicular to the plane along which the ultrasonic vibrating elements 2-1 to 2-7 are arranged, and FIGS. 5B and 5C show examples in which ultrasonic beams 32b and 32c are directed to the right hand side and the left hand side, respectively. In these figures, reference numerals 30a, 30b and 30c denote equi-phase planes, and 31a, 31b and 31c represent memories for storing sampled data in accordance with a distance. In the drawings, there are provided plural memories the number of which is equal to the number of equi-phase planes. In practice, a much greater number of memories are provided. By changing the equi-phase planes in various manners, it is possible to attain any desired directivity of the ultrasonic beam.

In the present embodiment, the reading-out of the address for the wave surface memory unit 17 is controlled by the address control circuit 18 to obtain a desired equi-phase plane and the thus derived wave surface data is processed to obtain the ultrasonic reflection image. That is to say, after all the wave surface data corresponding to the ultrasonic vibrating elements 2-1 to 2-7 has been stored in the wave surface memory unit 17, the reading-out of the address is controlled by the address control circuit 18 such that wave surface data g(x) on a given equi-phase plane can be read-out. This wave surface data g(x) is then supplied to the FFT 19 and a spectrum distribution G(ω) representing the spatial frequency is derived in accordance with the following equations:

$$G(\omega) = \int_{-L/22}^{L/22} g(x) e^{-j\omega x} dx \quad (2)$$

$$G(\omega) = A(\omega) + jB(\omega) \quad (3)$$

$$P(\omega) = \sqrt{A^2(\omega) + B^2(\omega)} \quad (4)$$

$$\theta(\omega) = \tan^{-1} \frac{B(\omega)}{1A(\omega)} \quad (5)$$

wherein L is a length of the ultrasonic probe 1, P(ω) a power spectrum and θ(ω) denotes a phase spectrum.

As can be understood from the above explanation, the wave surface data g(x) is composed of real part data A1 to A7(a(x)) and imaginary part data B1 to B7(b(x)), so that by deriving the spectrum distribution G(ω) with the aid of the FFT 19, it is possible to obtain the power spectrum P(ω) and phase spectrum θ(ω) from the real and imaginary parts A(ω) and B(ω) of the spectrum distribution in accordance with the above equations (4) and (5).

In the embodiment shown in FIG. 1, an output signal having a power spectrum distribution is obtained from FFT 19 in which a clutter signal component reflected by the stationary living tissues and a component reflected by the blood stream are superimposed one upon the other. If the relative movement between the living tissues and the ultrasonic probe is zero, the clutter component reflected by the stationary living tissues contains dominantly a DC component as shown in FIG. 6A. However, when relative movement occurs between the ultrasonic probe and the living tissues due to breathings, a frequency axis is deviated by a Doppler frequency corresponding to the relative movement as illustrated in FIG. 6B. In this case, the magnitude of the reflection signal from the blood stream is always smaller than that of the reflection signal from the living tissues (i.e. the clutter component) by 40 to 50 dB, so that the maximum value of the output signal from the FFT 19 always indicates the clutter component.

Therefore, when a component higher than a cut-off frequency $f_c$ shown by a chain line is derived, the clutter component is erroneously extracted in the case in which the relative movement between the ultrasonic probe and the living tissues occurs as shown in FIG. 6B. This results in that the velocity of the blood stream can not be detected accurately. However, when the relative movement does not occur, the Doppler frequency component due to the blood stream can be correctly extracted as illustrated in FIG. 6A.

In order to remove the above mentioned drawback, in the present embodiment, at first a peak frequency $f_o$ of the spectrum distribution is detected by a peak detection circuit 20. It should be noted that the clutter signal has the peak, and thus the peak frequency $f_o$ indicates the Doppler frequency due to the relative movement between the ultrasonic probe and the living tissues. Then, the frequency axis of the power spectrum distribution is shifted in a frequency axis shift circuit 21 such that the peak frequency $f_o$ becomes zero as shown in FIG. 6C.

In the case of detecting the peak frequency $f_o$ at which the clutter component shows its peak, respective spaces in which the focus points are formed by the wave surface synthesizing method may be selected. However, in order to detect the peak frequency $f_o$ in a more reliable manner, after averaging frequency spectrum components obtained for respective spaces in the same direction, a peak frequency of the averaged frequency spectrum component is derived. In this manner, the peak frequency can be detected optimally by utilizing a phenomenon that relative movement due to the movement of the ultrasonic probe appears in the same manner in respective directions of the composed beams.

Next the power spectrum distribution corrected by the frequency axis shift circuit 21 is supplied to a discriminated peak detection circuit 22. In this discriminated peak detection circuit 22, a frequency component which is lower than the cut-off frequency $f_c$ is extracted as the B-mode image signal and a frequency component equal to or higher than the cut-off frequency $f_c$ is extracted as the Doppler signal component corresponding to the blood stream. In the present embodiment, the peak frequency $f_o$ at which the power spectrum distribution produced by the FFT 19 becomes maximum is detected by the peak detection circuit 20, the power spectrum distribution is shifted in the frequency axis shift circuit 21 such that the peak frequency $f_o$ becomes zero, and then the B-mode signal component and the Doppler signal component can be simply and accurately discriminated in the discriminated peak detection circuit 22 by using a filter having cut-off frequency $f_c$. In this manner, the Doppler signal due to the blood stream can be effectively detected without being influenced by the relative movement between the ultrasonic probe and the living tissues.

After the Doppler signal component has been extracted in the manner explained above, the Doppler frequency can be detected by deriving an average frequency $f_d$ from the spectrum component in accordance with the following equation:

$$f_d = \frac{\int_{f_c}^{\infty} f \cdot G(f) df}{\int_{f_c}^{\infty} G(f) df} \quad (6)$$

In practice, the blood stream has a two-dimensional velocity component, so that the power spectrum distribution $P(\omega)$ and phase spectrum $\theta(\omega)$ have various patterns. However, a velocity component parallel with the ultrasonic probe can be detected by utilizing the symmetry of the positive and negative frequency components in the power spectrum distribution. For instance, when the blood stream moves toward the ultrasonic probe and at the same time the living tissues move toward the ultrasonic probe, the power spectrum distribution is shifted in a higher frequency direction as shown in FIG. 6, but when only the living tissues move away from the ultrasonic probe, the peak of the spectrum component due to the living tissues appears in the negative frequency range. Then, the power spectrum distribution is shifted toward the higher frequency side by the peak frequency. When the blood stream moves away from the ultrasonic probe and the living tissues move toward the ultrasonic probe, the peak frequency due to the living tissues appears in the positive frequency range, but the peak frequency due to the blood stream appears in the negative frequency range. In such a case, frequency axis of the power spectrum distribution is shifted toward the negative frequency side such that the peak frequency due to the living tissues becomes zero. Therefore, according to the invention, the Doppler frequency due to the blood stream can be detected by extracting the power spectrum components outside the cut-off frequency range from $-f_c$ to $+f_c$.

In the present embodiment, the velocity components of the blood stream, i.e., the magnitude and direction of the blood stream are displayed in different colors. That is to say, the blood stream component toward the ultrasonic probe 1 (positive frequency component) is displayed in red, the blood stream component away form the ultrasonic prove, i.e., the negative frequency component is displayed in blue, and the blood stream component parallel with the ultrasonic probe (positive and negative frequency components) is displayed in green. These component signals are processed by the digital scan converter, and then are supplied to RGB inputs of the color monitor to which the B-mode image signal is also supplied. Therefore, the blood stream image is displayed in superimposition upon the B-mode image on the color monitor. In this manner, the two-dimensional blood stream can be displayed as the change in the hue, although the right and left directions could not be exactly expressed.

In the above embodiment, the ultrasonic probe 1 is formed by seven vibrating elements 2-1 to 2-7, but in practice the number of the vibrating elements is more than seven. For instance, the ultrasonic probe may be constructed by sixty four vibrating elements. By increasing the number of the ultrasonic vibrating elements, the directivity of the ultrasonic beam can be increased and the spatial resolution can be further improved. Moreover, a time period for the transmission and reception sequences for obtaining the reflection image at a certain point is made longer, and therefore it is possible to detect a blood stream having a very low velocity. Further, an amount of data is increased, and thus the Doppler frequency can be detected much more accurately.

In the above explained embodiment, the ultrasonic vibrating elements are arranged linearly to perform the electronic linear scan, but according to an invention they may be arranged along a circle or convex instead of the rectilinear arrangement. In case of using such an arrangement, the equi-phase sampling may be equally performed by suitably adjusting the sampling timings with the aid of the address control circuit 18.

FIG. 8 is a block diagram showing another embodiment of the ultrasonic diagnosing apparatus according to the invention, in which a number of ultrasonic vibrating elements of an ultrasonic probe 1—1 are arranged side by side along a circle to perform the electronic radial scan and the probe is arranged within the distal end of the insertion section of the endoscope. The distal end of the insertion section of the endoscope is inserted into a stomach 33 and the vibrating elements of the ultrasonic probe are successively driven to effect the electronical radial scan. Then, an ultrasonic sectional image of a stomach wall 32 can be observed. The remaining construction of the ultrasonic diagnosing apparatus of the present embodiment is entirely the same as the first embodiment illustrated in FIG. 1. In this apparatus, it is very difficult to fix the distal end of the insertion section within the stomach 33, and thus relative movement between the ultrasonic probe and the living tissues can not be avoided. Therefore, the above mentioned solution for removing the influence of the relative movement is very effective.

Figure 9A:
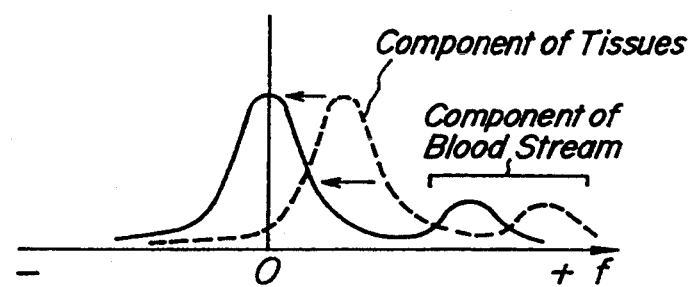
FIGS. 9A and 9B are schematic views depicting frequency spectra at various positions on the circularly arranged ultrasonic vibrating elements.
Figure 9B:
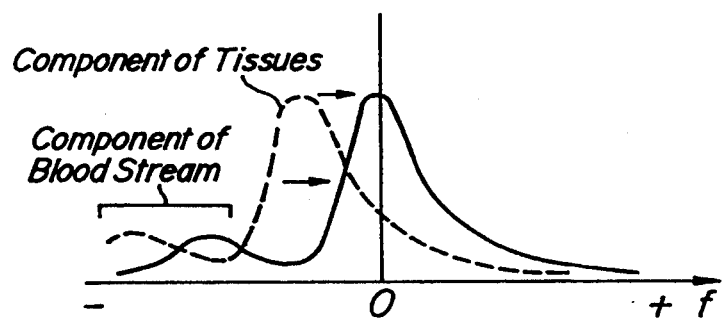

In FIG. 8, the ultrasonic probe 1—1 moves from a position shown by a broken line to a position illustrated by a solid line. In this case, there are produced a positive Doppler component at a point [A] and a negative Doppler component at a point [B] due to the relative movement of the ultrasonic probe and the living tissues. FIGS. 9A and 9B represent such a condition in relation to the frequency spectrum. FIG. 9A shows the frequency spectrum at the point [A] and FIG. 9B denotes the frequency spectrum at the point [B]. In FIGS. 9A and 9B, broken curves show the frequency spectra prior to the correction for the relative movement and solid curves express the frequency spectra after the correction. As can be clearly understood from these curves, a Doppler component of the clutter component in a certain synthesized ultrasonic beam direction has the same magnitude, but opposite sign with respect to that of a synthesized ultrasonic beam which is opposite to the direction with respect to the circularly arranged ultrasonic probe.

In the present embodiment, the movement of the ultrasonic probe 1—1 is compensated for in all the directions of the synthesized ultrasonic beam in the same manner as that has been described in the first embodiment, and thus the frequency spectrum which is free from the movement of the ultrasonic probe can be obtained. Therefore, the Doppler component only due to the blood stream can be detected.

In the so far explained embodiments, the peak frequency of the component reflected by the living tissues is detected from the power spectrum distribution obtained by the FFT 19, the frequency axis of the power spectrum distribution is shifted such that the detected peak frequency becomes zero, and then the Doppler frequency component which is not influenced by the relative movement between the ultrasonic probe and the living tissues is extracted from the power spectrum component part outside the cut-off frequency range from $-f_c$ to $+f_c$. However, according to the invention, it is not always necessary to effect the frequency axis shift.

FIG. 10 is a part of an embodiment of the ultrasonic diagnosing apparatus according to the invention. In the present embodiment, the power spectrum component obtained by the FFT 19 is supplied to a first peak frequency detection circuit 34 to detect a first peak frequency $f_o$ at which the power spectrum becomes maximum. The power spectrum component is also supplied to a second peak detection circuit 35 and a second peak frequency $f_{d'}$ is detected. Then, the thus detected first and second peak frequencies $f_o$ and $f_{d'}$ are supplied to a subtracting circuit 36 and a difference between the second peak frequency $f_{d'}$ and the first peak frequency $f_o$ is derived. In almost all cases, the second peak frequency $f_{d'}$ corresponds to the blood stream, and thus the difference frequency $f_d = f_{d'} - f_o$ represents the Doppler frequency of the blood stream from which the influence of the relative movement between the ultrasonic probe and the living tissues has been removed.

FIG. 11 is a block diagram showing another embodiment of the ultrasonic diagnosing apparatus according to the invention. The apparatus comprises ultrasonic probe 101, beam synthesizing circuit 102, transmitting signal generator 103, transmitting circuit 104, receiving amplifier 105, band pass filter (BPF) 106, multipliers 107a, 107b, local oscillation circuit 108, 90-degree phase shift circuit 109, A/D converters 110a, 110b, MTI filters 111a, 111b for transmitting only a high frequency component, auto-correlation circuit 112, velocity calculating circuit 113, control circuit 114 for controlling the MTI filters 111a, 111b, B-mode image receiving circuit 115, display device 116 for displaying the B-mode image and Doppler image, and cursor indicator 117.

In the present embodiment, a transmission signal is generated by the transmission signal generating circuit 103 at a predetermined repetition period $T_p$. After this transmission signal has been amplified by the transmitting circuit 104, the signal is supplied via the beam synthesizing circuit 102 to the ultrasonic probe 101 to emit an ultrasonic beam in a given direction. An ultrasonic wave reflected by objects under inspection is received by the probe 101 to generate an electric signal. This signal is supplied to the beam synthesizing circuit 102 to the B-mode image receiving circuit 115 and a B-mode ultrasonic sectional image is displayed on the display device 116 in usual manner. The signal produced by the ultrasonic probe 101 is also supplied to the receiving amplifier 105 and is amplified thereby to a suitable level. Then, after the amplified signal has been supplied to the BPF 106 to cut-off undesired signal components, the signal is supplied to the multipliers 107a and 107b.

From the local oscillator 108, there is produced a signal having the same frequency as that of the transmission signal. This signal is directly supplied to the multiplier 107a and is supplied via the 90-degree phase shift circuit 109 to the multiplier 107b. In this manner, the echo signal is orthogonally detected and is converted into a complex signal represented by real and imaginary parts. The complex signal components are then supplied to the A/D converters 110a and 110b and are sampled at the repetition period $T_p$ of the transmitting operation to obtain digital signals I and Q. These digital complex components correspond to the Doppler signal and its frequency component becomes larger in proportion to a velocity of the relative movement between the ultrasonic probe 101 and the living tissues.

The reflected ultrasonic wave includes not only a component reflected by the blood stream, but also components reflected by living tissues surrounding the blood stream. In the present embodiment, in order to extract the Doppler component due to the blood stream without being influenced by the components due to the living tissues, the output signals of the A/D converters 110a, 110b are supplied to the MTI (Moving Target Indicator) filters 111a and 111b, respectively. The MTI filter itself has been well known in the art and has been widely used to detect flying airplanes without being affected by the influence of buildings. In the medical field, the MTI filter is also called the WALL-filter which can remove the influence of walls of a heart of a patient. In the above mentioned Japanese Patent Application Laid-open Publication Kokai Sho 58-188433, the MTI filter is termed a delay line canceler.

FIG. 12 is a schematic view showing a condition in which the blood stream is measured from the outside of a patient body. A lung 120 is moved in accordance with the breathing of the patient, and thus the ultrasonic probe 101 provided on the patient body is also moved up and down. Therefore, an ultrasonic beam 118 is subjected to Doppler shifts due to not only a blood vessel 119, but also all near and far tissues. Then, the frequency spectrum of the Doppler signal includes not only a blood stream component, but also a clutter component as shown in FIG. 13A. In practice, a level of the component due to the reflection by the living tissues is usually larger than that of the component due to the blood stream by 40 to 50 dB.

In the present embodiment, in order to extract only the blood stream component effectively, the MTI filters 111a and 111b are selectively turned on and off. It should be noted that when the MTI filter is turned off, the signal passes through the MTI filter as it is. In the auto-correlation circuit 112, an average frequency of the power spectrum distribution of the output signal generated by the A/D converters 110a and 110b when the MTI filters 111a and 111b are turned on is derived and an average frequency of the spectrum distribution when the MTI filters are turned off is derived. The thus derived average frequencies are supplied to the velocity calculating circuit 113. In this circuit 113, a true velocity of the blood stream which is not influenced by the movement of the ultrasonic probe 101 is calculated.

When the MTI filters 111a and 111b are turned off, the signal shown in FIG. 13A is supplied to the auto-correlation circuit 112. As stated above, the level of the power spectrum component due to the reflection of the living tissues is large than that due to the blood stream, and therefore the average frequency detected by the auto-correlation circuit 112 corresponds to the Doppler frequency $f_o$. When the MTI filters 111a and 111b are turned on, the power spectrum signal is subjected to the filtering operation shown in FIG. 13B, so that the low frequency power spectrum component due to the reflection of the living tissues is substantially removed and the average frequency corresponds to the Doppler frequency $f_v$ of the blood stream.

In the calculating circuit 113, for instance the Doppler frequency $f_o$ is subtracted from the Doppler frequency $f_v$ to derive a difference and then the difference is multiplied by a predetermined proportional coefficient to derive a velocity of the blood stream which is not affected by the movement of the ultrasonic probe 101. A distribution of the thus detected blood stream is displayed on the display device 116 in super-imposition upon the B-mode image generated by the output signal from the B-mode image receiving circuit 115 in the same manner as that of the previous embodiments.

In the embodiment just explained above, the transmission characteristics of the MTI filters 111a and 111b are fixed. However, according to the invention, the transmission characteristic of the MTI filter may be adjustable. That is to say, the cut-off frequency of the MTI filter may be changed in accordance with the Doppler frequency $f_o$ of the power spectrum component due to the living tissues such that the cut-off frequency is made higher when the Doppler frequency $f_o$ is high. By this measure, it is possible to suppress optimally the influence of the power spectrum component due to the reflection by the living tissues and the Doppler frequency due to the blood stream can be detected very accurately.

In the above explanation, the Doppler frequency is detected from the power spectrum obtained at all the measuring points, but in the present embodiment, the Doppler frequency due to the movement of the ultrasonic probe 101 may be detected for a reference point denoted by a cursor 121 in FIG. 12. The cursor 121 may be moved over the B-mode image by operating the cursor indicator 117. In this case, the cursor point 121 is important for obtaining the Doppler frequency due to the blood stream in an accurate manner, but the operation of the control circuit 114 may be simplified.

In the embodiment explained above, the Doppler frequencies $f_o$ and $f_v'$ due to the living tissues and blood stream are detected by selectively operating the MTI filters 111a and 111b in a time division manner, and thus a frame rate is decreased. In order to avoid such a drawback, in a modification of the embodiment shown in FIG. 11, a block A denoted by a broken line in FIG. 11 is constructed in a manner illustrated in FIG. 14.

Figure 14:
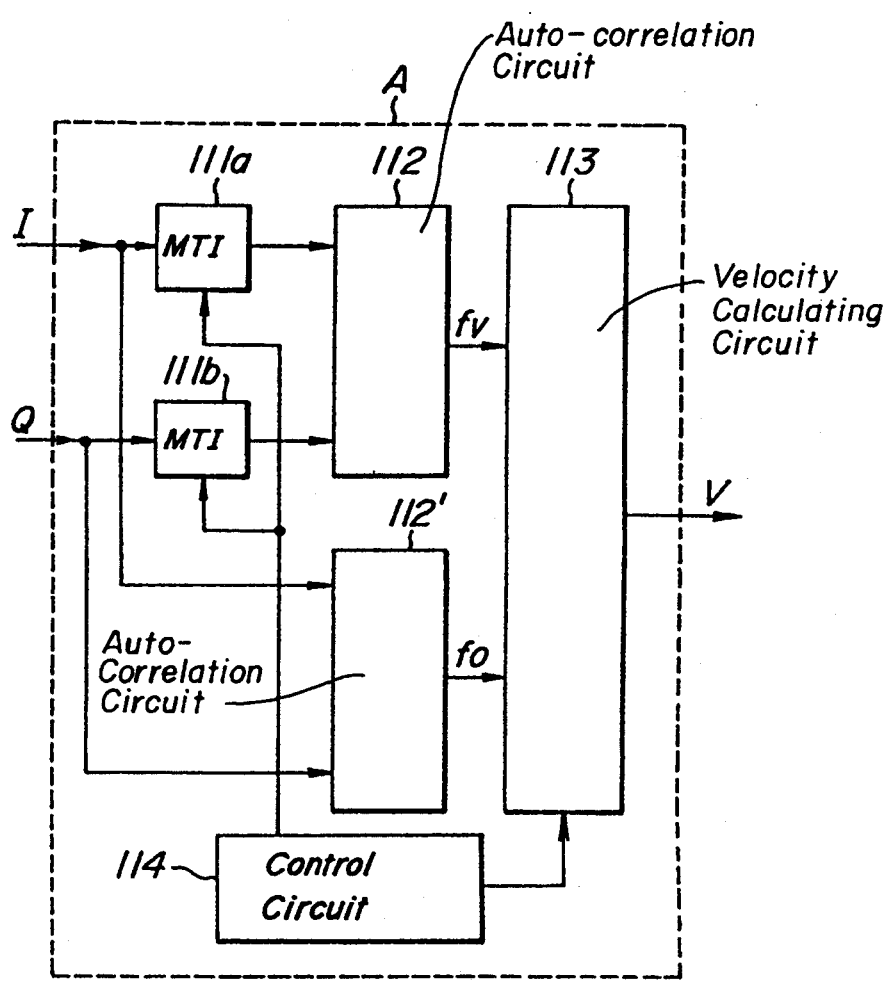
FIG. 14 is a block diagram showing a Doppler frequency detecting circuit in a modification of the embodiment illustrated in FIG. 11.

In the embodiment shown in FIG. 14, there are arranged first and second auto-correlation circuits 112 and 112' and the digital complex signals I and Q are supplied to the first auto-correlation circuit 112 via the MTI filters 111a and 111b. At the same time, the digital complex signals I and Q are directly supplied to the second auto-correlation circuit 112'. Therefore, the Doppler frequency $f_o$ due to the living tissues is detected by the first auto-correlation circuit 112 and the Doppler frequency $f_v$ due to the blood stream is detected by the second auto-correlation circuit 112'. The thus detected Doppler frequencies are supplied to the velocity calculating circuit 113 to detect the velocity of the blood stream without being influenced by the living tissues. In the present embodiment, the control circuit 114 controls the cut-off frequencies in accordance with the Doppler frequency $f_o$ due to the living tissue. In this manner, the Doppler frequencies $f_o$ and $f_v$ due to the living tissues and blood stream, respectively can be detected simultaneously by the first and second auto-correlation circuits 112 and 112', and therefore the velocity V of the blood stream free from the movement of the ultrasonic probe 101 can be derived without reducing the frame rate.

Figure 15:
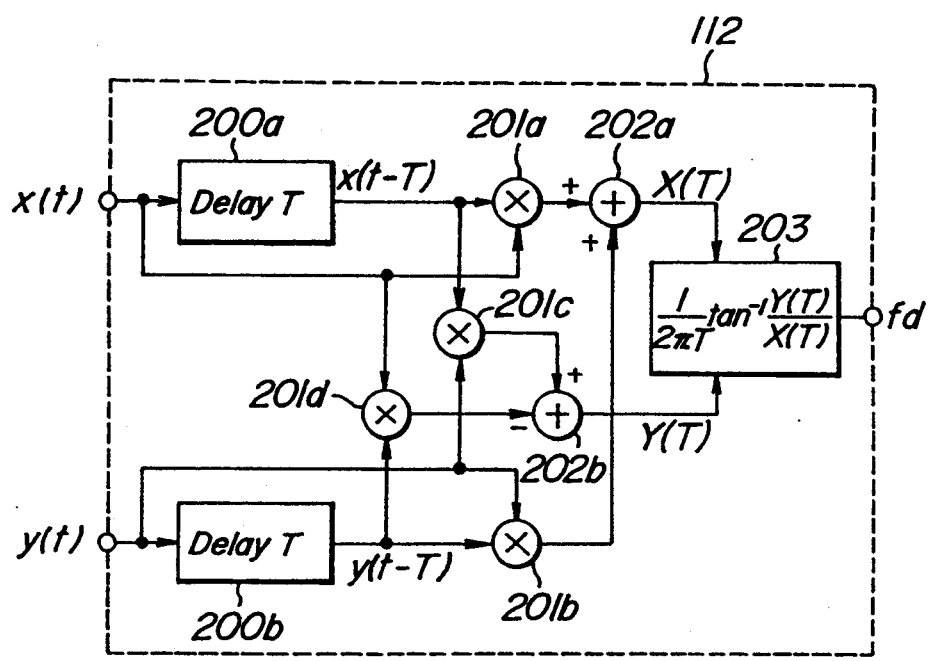
FIG. 15 is a block diagram depicting a detailed construction of an auto-correlation circuit shown in FIG. 11.

FIG. 15 is a block diagram showing the detailed construction of the auto-correlation circuit 112. The digital complex signals produced by the A/D converters 110a and 110b in FIG. 11 may be expressed by the following equation:

$$x(t)+jy(t)=e^{j2\pi f_d t} \quad (7)$$

wherein x(t) represents the real part, y(t) the imaginary part, and $f_d$ denotes the Doppler frequency. When a conjugate product of this complex signal and a complex signal $e^{j2\pi f_d(t-T)}$ which is obtained by delaying the complex signal $e^{j2\pi f_d t}$ by the transmission period T is derived in the following manner:

$$e^{j2\pi f_d t} \cdot e^{j2\pi f_d(t-T)} = e^{j2\pi f_d T} \quad (8)$$

This equation (8) may be changed as follows:

$$[x(t)+jy(t)]\cdot[x(t-T)-jy(t-T)]=x(t)x(t-T)+y(t)y(t-T)+j[y(t)x(t-T)-x(t)y(t-T)] \quad (9)$$

The above calculations are performed by delay circuits 200a, 200b, multipliers 201a~201d and adders 202a, 202b.

Now it is assumed that a real part of the above conjugate product is expressed by X(T) and the imaginary part is denoted by Y(T). Then, the Doppler frequency $f_d$ can be derived by the following equation in a phase deflecting circuit 203 due to the relation between the complex vector and the phase:

$$f_d = \frac{1}{2\pi T} \tan^{-1} \frac{Y(T)}{X(T)} \qquad (10)$$

Figure 16:
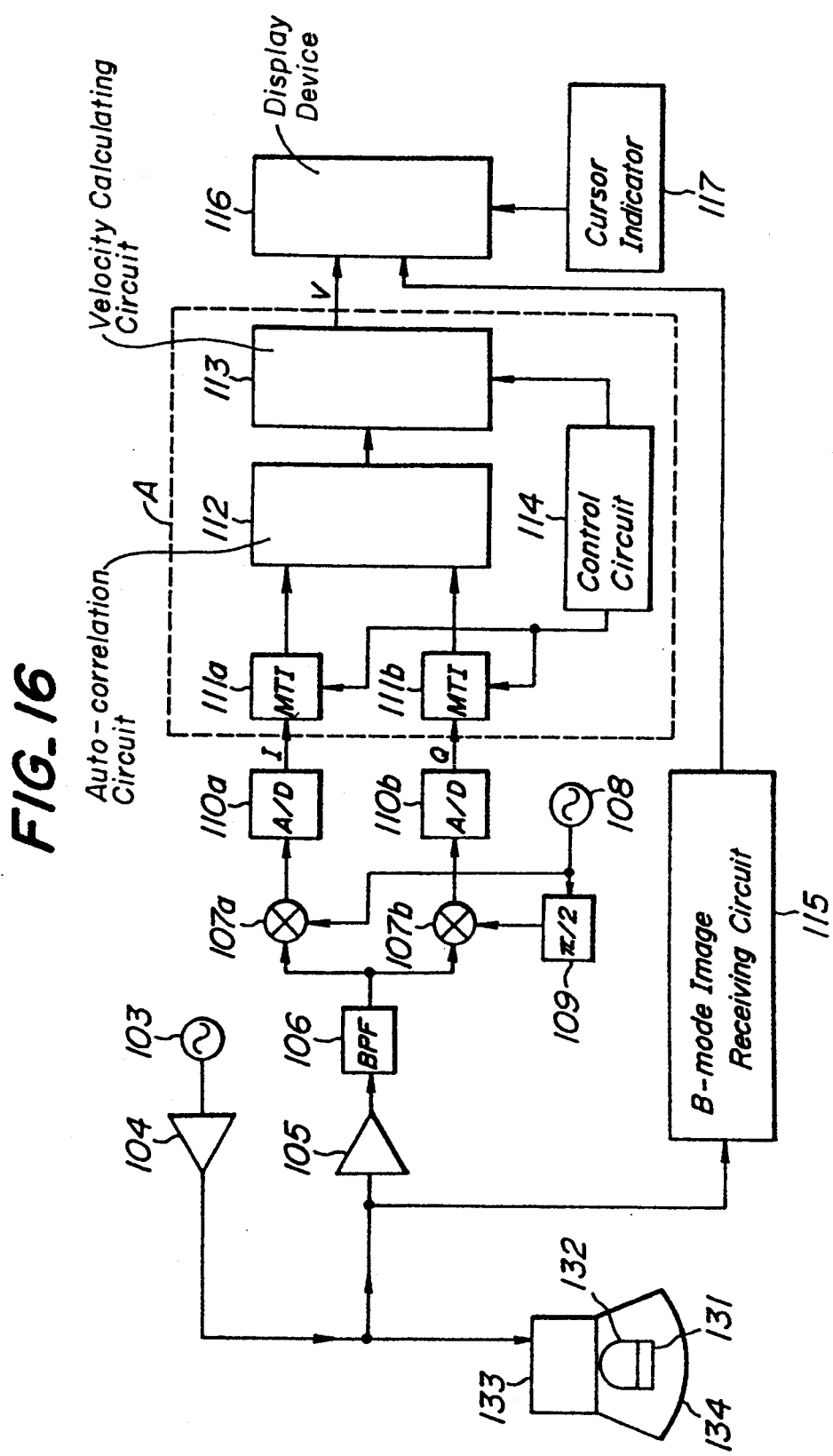
FIG. 16 is a block diagram showing another embodiment of the ultrasonic diagnosing apparatus according to the invention.

FIG. 16 is a block diagram showing a modification of the embodiment of the ultrasonic diagnosing apparatus according to the invention shown in FIG. 11. In the embodiment illustrated in FIG. 11, the ultrasonic probe 101 is formed by arranging a plurality of ultrasonic vibrating elements, but in the present embodiment only one ultrasonic vibrating element is provided and this element is moved mechanically to perform a mechanical sector scan. That is to say, a single ultrasonic vibrating element 131 is secured to a driving force transmission mechanism 132 and is rotated or swung by a driving mechanism 133 including an electric motor. The ultrasonic vibrating element 131 is arranged within a case having a cap 134 which can transmit the ultrasonic wave. The ultrasonic vibrating element 131 is electrically connected to the transmitting amplifier 104, receiving amplifier 105 and B-mode image receiving circuit 115. The remaining construction of the present embodiment is entirely the same as that of the embodiment illustrated in FIG. 11, and the manner of detecting the velocity of the blood stream is also identical with that of the embodiment of FIG. 11.

As explained above in detail, in the ultrasonic diagnosing apparatus according to the invention, the velocity of the blood stream can be accurately measured without being affected by the relative movement between the ultrasonic vibrating element and the living tissues surrounding the blood stream, so that the patient can be free from the load. In one embodiment of the ultrasonic diagnosing apparatus according to the invention, the wave surface data obtained by respective vibrating elements is stored in the wave surface memory and the thus stored wave surface data is sampled by adjusting the time axis such that a focal point is formed to derive the power spectrum, the frequency axis of the power spectrum is shifted such that the peak frequency due to the reflection by the living tissues becomes zero, and then the Doppler frequency due to the blood stream is detected from the frequency axis shifted power spectrum. In another embodiment of the ultrasonic diagnosing apparatus according to the invention, the Doppler frequency due to the living tissues is detected from the output signal of the MTI filter, the Doppler frequency due to the blood steam is detected from the echo signal which is not subjected to the filtering operation of the MTI filter, and then the velocity of the blood stream is calculated from the thus detected Doppler frequencies.

When the frequency axis is shifted, the power spectrum component due to the reflection by the living tissues and that due to the blood stream can be simply discriminated from each other by merely using the cut-off frequency. In this case, the cut-off frequency may be set to a lower frequency by correcting the movement of the ultrasonic probe, and thus the blood stream having a very low velocity can be detected at a high precision without reducing the power spectrum component of a low frequency range.

Moreover, the blood stream not only in the direction in which the ultrasonic beam propagates but also in the direction parallel with the beam propagating direction (in the direction parallel with the ultrasonic probe) can be detected from the pattern of the power spectrum distribution. When the thus detected velocity of the blood stream is displayed in color in super-imposition upon the B-mode ultrasonic sectional image on the color monitor, the condition of the blood stream can be easily perceived.

In the manner explained above, according to the present invention, the blood stream of very low velocity can be accurately detected and further the blood stream parallel with the ultrasonic probe can be also detected. Therefore, the present invention can be very advantageously applied to the ultrasonic endoscope in which the distal end of the insertion section is liable to move.

What is claimed is:

1. An ultrasonic diagnosing apparatus comprising:
    ultrasonic wave transmitting and receiving means including an ultrasonic probe having a plurality of ultrasonic vibrating elements arranged in an array for emitting ultrasonic waves, which are delayed by predetermined delay times, toward a living body and receiving ultrasonic waves reflected by the living body to produce an echo signal, said plurality of ultrasonic vibrating elements being successively driven to transmit ultrasonic pulses so as to produce a plurality of echo signals; and
    a signal processing circuit, for processing said echo signal generated from said ultrasonic wave transmitting and receiving means, comprising means for detecting a power spectrum distribution from said plurality of echo signals by a synthetic aperture method, means for detecting a Doppler frequency contained in the echo signal due to relative movement between said ultrasonic probe and living tissues of the living body in accordance with said power spectrum distribution, and means for determining a velocity of a blood stream within the living body in accordance with said Doppler frequency, such that said velocity is determined without being influenced by said relative movement between the ultrasonic probe and the living tissues.

2. An apparatus according to claim 1, wherein said signal processing means comprises means for detecting, as a first Doppler frequency, said Doppler frequency due to the relative movement between the ultrasonic probe and the living tissues, means for shifting a frequency axis of said power spectrum distribution such that said first Doppler frequency becomes zero to obtain a frequency axis shifted power spectrum distribution, means for detecting, as a second Doppler frequency, a Doppler frequency due to the blood stream from a power spectrum component in said frequency axis shifted power spectrum distribution which is out of a cut-off frequency range, and means for detecting said velocity of the blood steam from said second Doppler frequency.

3. An apparatus according to claim 2, wherein said means for detecting the second Doppler frequency due to the blood stream derives said velocity of the blood stream from an average frequency of said power spectrum component which is out of the cut-off frequency range.

4. An apparatus according to claim 1, wherein said signal processing means comprises means for detecting a first peak frequency of the power spectrum distribution of the echo signal as said first Doppler frequency, means for detecting a second peak frequency of the power spectrum distribution of the echo signal as said second Doppler frequency, means for detecting the Doppler frequency due to the blood stream by subtracting said first Doppler frequency from said second Doppler frequency, and means for calculating said velocity of the blood stream from said Doppler frequency due to the blood stream.

5. An apparatus according to claim 1, wherein the reflected ultrasonic waves are received by the ultrasonic vibrating elements to produce output signals and said output signals are delayed by predetermined delay times to produce the echo signals, and said signal processing means is constructed such that said echo signal is orthogonally detected to derive a complex signal, an auto-correlation of said complex signal is derived, said Doppler frequency due to the relative movement between the ultrasonic probe and the living tissues is detected from said complex signal, and said velocity of the blood stream which is free from the influence of the relative movement between the ultrasonic probe and the living tissues is detected on the basis of said Doppler frequency due to the relative movement between the ultrasonic probe and the living tissues.

6. An apparatus according to claim 1, wherein said ultrasonic probe is formed by a single ultrasonic vibrating element, and said ultrasonic wave transmitting and receiving means comprises means for mechanically scanning said single ultrasonic vibrating element, whereby the ultrasonic pulses are emitted toward the living body, while the ultrasonic vibrating element is mechanically scanned.

7. An apparatus according to claim 1, wherein said ultrasonic probe is formed to be insertable into a cavity of the living body.

8. An ultrasonic diagnosing apparatus comprising:
a group of a plurality of ultrasonic vibrating elements which are arranged in an array;
a switching circuit for switching said plurality of ultrasonic vibrating elements successively;
a transmitting circuit for supplying pulses to said group of the ultrasonic vibrating elements to emit ultrasonic waves therefrom;
a receiving circuit for amplifying an echo signal generated by an ultrasonic vibrating element which emits an ultrasonic wave and receives an ultrasonic wave reflected by a living body;
an orthogonal detection circuit for converting said echo signal into a complex signal;
A/D converters for converting the complex signal into digital complex signal;
a plurality of wave surface memories for storing a plurality of said digital signals for respective ultrasonic vibrating elements as complex wave surface data;
a power spectrum distribution detection circuit for detecting a power spectrum distribution on the basis of the complex wave surface data stored in said wave surface memories;
a peak detection circuit for detecting a peak frequency of said power spectrum distribution;
a frequency axis shift circuit for shifting a frequency axis of said power spectrum distribution such that said peak frequency becomes zero to produce a frequency axis shifted power spectrum distribution;
means for extracting a higher frequency component of said frequency axis shifted power spectrum distribution; and
means for detecting a velocity of a blood stream from said higher frequency component without being affected by a relative movement between said ultrasonic vibrating elements and living tissues of the living body.

9. An apparatus according to claim 8, wherein said group of the ultrasonic vibrating elements is constructed to be insertable into a cavity of the living body.

10. An ultrasonic diagnosing apparatus comprising:
a plurality of ultrasonic vibrating elements arranged in an array;
a beam synthesizing circuit connected to said ultrasonic vibrating elements for supplying signals having different phases to said ultrasonic vibrating elements to emit ultrasonic waves therefrom and for receiving and delaying echo signals generated by the ultrasonic vibrating elements which receive ultrasonic waves reflected by a living body;
a transmission circuit for supplying pulses via said beam synthesizing circuit to said ultrasonic vibrating elements;
a receiving circuit for amplifying the echo signal generated by the ultrasonic vibrating elements and being passed through said beam synthesizing circuit;
an orthogonal detection circuit for converting the echo signal supplied by said receiving circuit into an complex signal:
A/D converters for converting said complex signal into a digital complex signal;
MTI filters for filtering said digital complex signal, said MTI filters having variable cut-off frequencies adjustable in response to a control signal;
means for detecting from output signals generated by said MTI filters a first Doppler frequency due to a blood stream;
means for detecting from the digital complex signal which is not processed by the MTI filters a second Doppler frequency due to a reflection by living tissues in the living body;
means, operatively associated with said MTI filters and for generating said control signal in accordance with said second Doppler frequency;
means for detecting a third Doppler frequency which is not affected by a relative movement between the ultrasonic vibrating elements and the living tissues as a difference between said first and second Doppler frequencies; and
means for detecting a velocity of the blood stream from said third Doppler frequency.

11. An apparatus according to claim 10, wherein said group of the ultrasonic vibrating elements is constructed to be insertable into a cavity of the living body.

12. An apparatus according to claim 10, wherein said means for detecting a first Doppler frequency comprises a first autocorrelation circuit connected to said MTI filters; and
said means for detecting a second doppler frequency comprises a second autocorrelation circuit connected to said A/D converters.

13. An apparatus according to claim 1, wherein said means for detecting a Doppler frequency comprises means for detecting a first peak frequency in said frequency power spectrum, wherein said first peak frequency is determined to be said Doppler frequency.

14. An apparatus according to claim 13, wherein said means for determining a velocity of a blood stream comprises:

means, receiving said frequency power spectrum and said first peak frequency, for (i) frequency shifting said frequency power spectrum in response to said first peak frequency, (ii) extracting frequency components of said frequency power spectrum, which are lower than a predetermined cut-off frequency, as B-mode image data, and (iii) determining said velocity of the blood stream based on frequency components of said frequency power spectrum which are equal to or less than said cut-off frequency.

15. An apparatus according to claim 13, wherein said means for determining a velocity of a blood stream comprises:

means, receiving said frequency power spectrum and said first peak frequency, for (i) detecting a second peak frequency in said frequency power spectrum, and (ii) comparing said first peak frequency and said second peak frequency so as to determine said velocity of the blood stream.

16. An apparatus according to claim 15, wherein said means for comparing said first peak frequency and said second peak frequency comprises means for subtracting said second peak frequency from said first peak frequency.

17. An ultransonic diagnosing apparatus comprising:
(a) ultrasonic wave transmitting and receiving means including an ultrasonic probe for emitting ultrasonic waves toward a living body and receiving ultrasonic waves reflected by the living body to produce an echo signal; and
(b) a signal processing circuit, for processing said echo signal generated from said ultrasonic wave transmitting and receiving means, comprising
(i) means for converting said echo signal into a complex signal,
(ii) MTI filters, receiving said complex signal, for filtering said complex signal and outputting a filtered complex signal,
(iii) first autocorrelation means, connected to receive said complex signal, for detecting a first Doppler frequency contained in the complex signal due to relative movement between said ultrasonic probe and living tissues of the living body, and
(iv) second autocorrelation means, connected to receive said filtered complex signal, for detecting a second Doppler frequency due to reflection by a blood stream in said living body, and
(v) means for determining a velocity of said blood stream in accordance with said first Doppler frequency and said second Doppler frequency, such that said velocity is determined without being influenced by said relative movement between the ultrasonic probe and the living tissues.

18. An apparatus according to claim 17, wherein said ultrasonic probe comprises a single ultrasonic vibrating element, and said ultrasonic wave transmitting and receiving means further comprises means for mechanically scanning said single ultrasonic vibrating element.

19. An ultrasonic diagnosing apparatus comprising:
ultrasonic wave transmitting and receiving means including an ultrasonic probe having a plurality of ultrasonic vibrating elements arranged in an array for emitting ultrasonic waves, which are delayed by predetermined delay times, toward a living body and receiving ultrasonic waves reflected by the living body to produce an echo signal, said plurality of ultrasonic vibrating elements being successively driven to transmit ultrasonic pulses and to produce a plurality of echo signals; and
a signal processing circuit for processing said echo signals generated from said ultrasonic wave transmitting and receiving means, said signal processing circuit comprising means for detecting a power spectrum distribution from said plurality of echo signals by a synthetic aperture method, means for detecting a Doppler frequency contained in the echo signals due to relative movement between said ultrasonic probe and living tissues of the living body in accordance with said power spectrum distribution, means for determining a Doppler frequency of a blood stream within the living body by removing a spectrum component due to the living tissues from the echo signals, means for deriving a difference frequency between the Doppler frequency due to the relative movement between the ultrasonic probe and the living tissues and the Doppler frequency due to the blood stream, and means for detecting a velocity of the blood stream from said difference frequency without being influenced by said relative movement between the ultrasonic probe and the living tissues.

20. An apparatus according to claim 19, wherein said signal processing means comprises means for detecting a first Doppler frequency as an average frequency of the power spectrum of the echo signal and a second Doppler frequency by removing from a reflection signal a power spectrum component corresponding to a signal component reflected by the living tissues, and means for detecting said velocity of the blood stream on the basis of a difference between said first and second Doppler frequencies.

21. An apparatus according to claim 20, wherein said means for detecting the first and second Doppler frequencies comprises first and second MTI filters which receive real and imaginary parts of said complex signal, respectively, a control circuit for selectively operating said first and second MTI filters, and an auto-correlation circuit for receiving output signals from said first and second MTI filters and generating said first and second Doppler frequencies successively.

22. An apparatus according to claim 21, wherein each of said MTI filters has a variable cut-off frequency and the second Doppler frequency is detected by changing the cut-off frequency in accordance with said first Doppler frequency.

23. An apparatus according to claim 20, wherein said means for detecting said first and second Doppler frequencies comprises a first auto-correlation circuit for receiving the real and imaginary parts of the complex signal and detecting said first Doppler frequency, first and second MTI filters for receiving the real and imaginary parts of the complex signal, respectively, and a second auto-correlation circuit for receiving output signals from said first and second MTI filters and detecting said second Doppler frequency.

24. An apparatus according to claim 23, wherein each of said MTI filters has a variable cut-off frequency and the second Doppler frequency is detected by changing the cut-off frequency in accordance with said first Doppler frequency.

25. An ultrasonic diagnosing apparatus comprising:
ultrasonic wave transmitting and receiving means including an ultrasonic probe for emitting ultrasonic waves toward a living body and receiving ultrasonic waves reflected by the living body to produce an echo signal; and a signal processing circuit for processing said echo signal generated from said ultrasonic wave transmitting and receiving means, said signal processing circuit comprising means for detecting a Doppler frequency contained in the echo signal due to relative movement between said ultrasonic probe and living tissues of the living body from a maximum signal peak level component of said echo signal or an average frequency of a power spectrum of said echo signal, means for determining a Doppler frequency of a blood stream within the living body by removing a spectrum component due to the living tissues from the echo signal, means for deriving a difference frequency between the Doppler frequency due to the relative movement between the ultrasonic probe and the living tissues and the Doppler frequency due to the blood stream, and means for detecting a velocity of the blood stream from said difference frequency without being influenced by said relative movement between the ultrasonic probe and the living tissues.

* * * * *